US008246416B2

(12) United States Patent
Frye

(10) Patent No.: US 8,246,416 B2
(45) Date of Patent: *Aug. 21, 2012

(54) COMFORT BRA LINER

(76) Inventor: Donna J. Frye, Laguna Hills, CA (US)

( * ) Notice: Subject to any disclaimer, the term of this patent is extended or adjusted under 35 U.S.C. 154(b) by 424 days.

This patent is subject to a terminal disclaimer.

(21) Appl. No.: 12/573,306

(22) Filed: Oct. 5, 2009

(65) Prior Publication Data

US 2010/0101586 A1  Apr. 29, 2010

Related U.S. Application Data

(63) Continuation-in-part of application No. 12/366,132, filed on Feb. 5, 2009, now Pat. No. 7,793,358, which is a continuation-in-part of application No. 12/257,975, filed on Oct. 24, 2008, now Pat. No. 7,794,304.

(51) Int. Cl.
*A41C 3/00* (2006.01)
*A41D 27/12* (2006.01)

(52) U.S. Cl. ............................................. 450/37; 2/46
(58) Field of Classification Search ............... 450/37, 450/54–58, 1, 81, 36; 2/51–53, 267, 268, 2/46, 56, 57, 455, 463, 50, 60
See application file for complete search history.

(56) References Cited

U.S. PATENT DOCUMENTS

| 2,534,721 A * | 12/1950 | Marshall ...................... 450/36 |
| 2,622,244 A | 12/1952 | Alberts |
| 2,641,763 A * | 6/1953 | Schroeder .................... 450/54 |
| 2,863,460 A * | 12/1958 | Monroe ........................ 450/11 |
| 2,869,552 A * | 1/1959 | Smith ............................ 450/32 |
| 3,642,009 A | 2/1972 | Nobbs |
| 3,701,168 A | 10/1972 | Balow |
| 3,763,865 A | 10/1973 | Defru |
| 2,698,940 A | 11/1995 | Dombeck |
| 5,573,441 A * | 11/1996 | Smith ........................... 450/89 |
| 5,603,653 A | 2/1997 | Hartman |
| 5,980,359 A * | 11/1999 | Brown ......................... 450/57 |
| 5,996,120 A * | 12/1999 | Balit ................................ 2/67 |
| 6,203,399 B1 * | 3/2001 | Hackney ........................ 450/1 |
| 6,264,530 B1 * | 7/2001 | Cosentino ................... 450/57 |
| 6,544,100 B1 | 4/2003 | Nadsady |
| 6,685,535 B2 | 2/2004 | Mitchell |
| 7,201,629 B2 * | 4/2007 | Lambru ........................ 450/1 |
| 7,585,200 B1 * | 9/2009 | McLaren ..................... 450/89 |
| 7,793,358 B2 * | 9/2010 | Frye ............................... 2/54 |
| 7,794,304 B2 * | 9/2010 | Frye ........................... 450/37 |
| 2005/0164602 A1 | 7/2005 | Armstrong et al. |
| 2008/0051005 A1 | 2/2008 | Huang |

* cited by examiner

*Primary Examiner* — Gloria Hale
(74) *Attorney, Agent, or Firm* — Stetina Brunda Garred & Brucker

(57) ABSTRACT

A foldable one-piece insert (i.e., bra liner) worn between the bra and the body having irritation reducing and/or absorbent material portions which line the bra cup and that lie under the supported breast, and portions which extends toward the torso rear under the bra side straps and a portion extending below the bra line along the torso. The invention further includes a material tab disposed between the material portions lining the bra cups, which can optionally be worn up to bridge the area between the bra cups for added protection, comfort and absorption of perspiration, or be folded down and out of sight when worn with lower cut neckline outer garments. A braless liner may also be used without a bra. The braless liner may be fastened to the female torso at the rear of the female torso with attachment mechanisms.

19 Claims, 5 Drawing Sheets

COMFORT BRA LINER

CROSS-REFERENCE TO RELATED APPLICATIONS

This application is a Continuation in part Application of U.S. Non-Provisional application Ser. No. 12/366,132, filed on Feb. 5, 2009 now U.S. Pat. No. 7,793,358 which is a continuation in part application of U.S. Non-Provisional application Ser. No. 12/257,975 filed Oct. 24, 2008 now U.S. Pat. No. 7,794,304, the entire disclosures of which are expressly incorporated herein by reference.

FIELD OF THE INVENTION

The present invention relates to bra liners and braless liners. By way of example and not limitation, the liners may have a contoured profile to provide selective contact with the body when used with or without conventional bras.

BACKGROUND OF THE INVENTION

Wearers of bras experience sores, rashes, skin tags and irritation under the breast resulting from perspiration and skin-to-skin contact. Furthermore, conventional bra construction offers little to address this problem area, having a material or construction which are designed for esthetic concerns. Additional discomfort arises in areas under the bra peripherally related to the breast such as under the side straps, and in areas adjacent to the bra, such as immediately below the bra line along the torso.

Moreover, for females that do not wear a bra, they do not have an appropriate alternative.

For the foregoing reasons, there is a need in the art for a device to provide comfort to females when wearing a bra and when braless.

SUMMARY OF THE INVENTION

The bra liner accordingly to the present invention provides a foldable one-piece insert worn between the bra and the body having irritation reducing or absorbent material portions which line the bra cup and that lie under the supported breast, and portions which extends toward the torso rear under the bra side straps, and a portion extending below the bra line along the torso.

A further feature includes a material tab disposed between the bra cup liners which can optionally be worn up to bridge the area between the bra cups for added protection, comfort and absorption of perspiration, or be folded down and out of sight when worn with lower cut neckline outer garments.

A still further feature according to the present invention provides removable inserts which are retained within the bra cup by material associated with the bra cup liner to help prevent dislocation of the inserts, which may comprise additional irritation reducing or absorbent material which may be desirable for comfort after surgery or exercise. Inserts also include appropriately shaped structures which provide lift, support, protection or esthetic enhancement.

A still further feature includes a curved front edge of the cup liner portions which are shaped to lie under the breast while avoiding contact with the breast nipple and areola areas to reduce of potential irritation to allow convenient breast feeding.

When worn, the bra liner according to one aspect of the present invention is foldable with one portion including the cup liners being placed in the bra cups, and a second portion which is unfolded and placed below the bra under the bra cups. Additional members extend from the cup liners and are placed between the bra straps and the wearer. The bra liner may be adjusted by the wearer to separate skin-to-skin contact and otherwise positioned between the bra and the torso for the desired comfort and/or absorption not possible with the bra. While worn, the material tab between the cup liners may be revealed by folding up, between the bra cups, or down, and inserts may be added or removed as desired.

The liner may also be worn without a bra. To this end, the liner may be secured to the female torso in a similar manner compared to a typical bra. By way of example and not limitation, the portions which extend toward the torso rear under the bra side straps may reach behind the back of the female torso and be removeably attachable to each other such as by hooks and eyelets, hooks and loops, buttons and button holes, snaps or adhesives. Alternatively, the portions may be permanently attached to each other by sewing.

BRIEF DESCRIPTION OF THE DRAWINGS

Various objects, features, and attendant advantages of the present invention will become more fully appreciated as the same become better understood when considered in conjunction with the accompanying drawings, in which like reference characters designate the same or similar part throughout the several view, and wherein.

DETAILED DESCRIPTION

Figure 1:
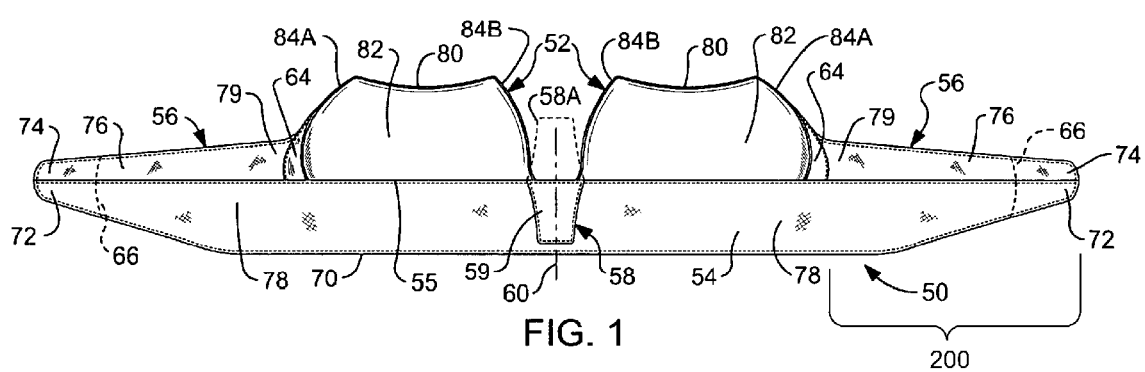
FIG. 1 is a rear elevation view of one embodiment of the present invention.
Figure 2:
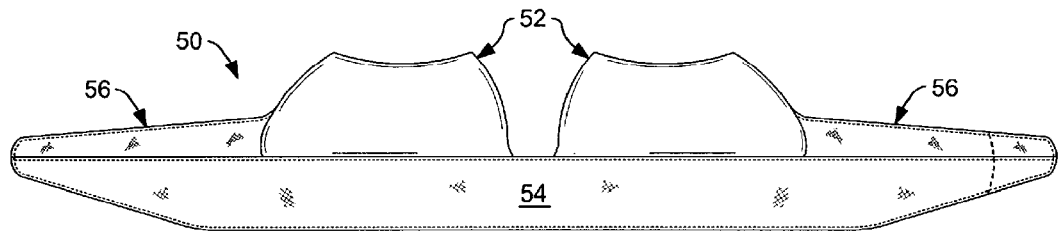
FIG. 2 is a front elevation view of the embodiment of FIG. 1.
Figure 3:
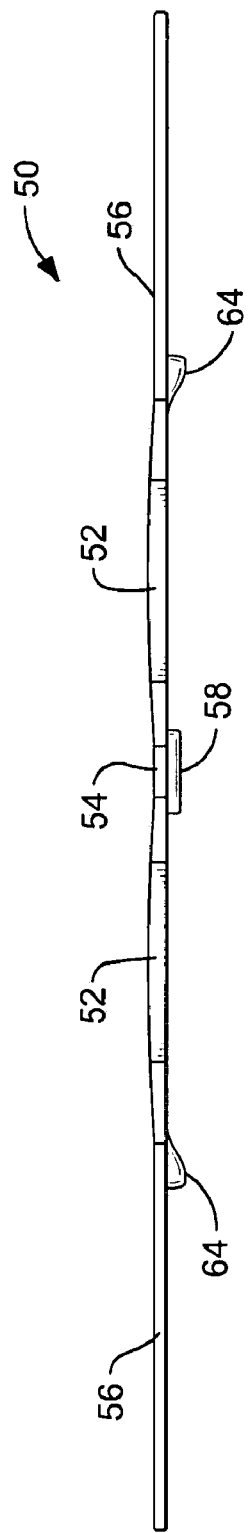
FIG. 3 is a plan view of the embodiment of FIG. 1.

With the construction of a typical bra being understood, an exemplary embodiment of a bra liner 50 according to the present invention is shown in FIGS. 1-3, including cup liners 52 which the wearer inserts into the bra and places under the breast, is attached to a strip 54 which retains the cup liners 52 in relative position and generally symmetrically outward from a midline 60, and when worn extends at least partially below the bra to be generally disposed over and at least partially in contact the body adjacent to the breast area to provide additional comfort and/or absorption in that area as well. The exemplary bra liner 50 further includes material bands 56 extending from the cup liner 52 parallel and include edges 76 connected to the edge 78 of strip 54 toward the ends thereof to form a foldable seam 55 with an opposing edge 70.

In the exemplary embodiment of the bra liner 50, both the bands 56 and the strip 54 have outer ends 74 and 72 respectively, terminating at substantially the same distance from the midline 60, but alternate embodiments may have either band (s) 56 or strip 54 extend farther. Typically, the bands 56 extend at least partially under the bra side straps (not shown) when in use. Furthermore, for applications where the bra liner 50 is to be worn to more completely encircle the body of the wearer, at least the bands 56 (and optionally the ends 72 of strip 54) can extended further along the bra straps to extend further around the torso of the wearer, and in some embodiments, touch or overlap each other, as discussed below in greater detail. Alternately, embodiments having a shorter terminus 66 of the bands 56 and/or strip 54 may be provided.

The cup liners 52 typically each have an arcuate edge 80 substantially opposite the edge 82 which edge 82 joins the strip 54 at seam 55, and further that arcuate edge 80 is generally shorter than edge 82 comprising material shaped or sufficiently pliant to conform to the bra cup when worn by the wearer. The edges 80 and 82 are connected by outer side 84A and inner side 84B, which are shaped to conform to provide the desired function as described above. The outer sides 84A are typically connected to the inner ends 79 of bands 56. The specific dimensions of the cup liner width between edges 80 and 82, as well as the shape or radius of the arcuate (e.g., concave) edge 80 is scaled according to the size of the wearer and corresponding bra, and dimensioned to substantially avoid contact with the breast nipple and if desired, the areola as well when placed in the bra. It is also contemplated that the edge 82 may be straight or convex.

An optional material tab 58 as shown in FIG. 1, has an edge 59 connected to the strip 54 edge 78 and is foldable thereon from a 'down' position as shown overlaying the strip 54, to an 'up' position 58A where it at least partially overlaps the cup insert 52 inner edges 84B. It is also contemplated that the bra liner 50 does not incorporate the material tab 58. In the exemplary embodiment shown, the cup inserts are separated with an intervening space between inner edges 84A, and the present embodiment bridges at least a portion of that space. The tab 58 may be pulled up (58A) for protection, absorption and comfort as needed.

Figure 4:
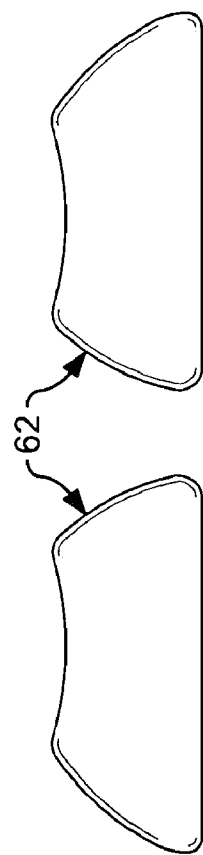
FIG. 4 is an elevation view of exemplary inserts as may be applied to the embodiment of FIG. 1.

Exemplary optional inserts 62, as shown in FIG. 4, may be applied to the present invention, and by reference to the exemplary embodiment 50 of FIGS. 1-3, generally retained on the cup liner 52 with optional flaps 64 shown in FIG. 1, which flaps 64 have outer edges connected to the cup liner outer edges 84a and lower edges connected to the cup liner 52 lower edge 82 to form a pouch to receive an edge, side, end, margin or other portion of the inserts 62 when worn by the wearer. The inserts are selected by the wearer to provide additional protection, to reduce irritation, to enhance absorption, to provide support, lift, and esthetic improvement (including prosthesis) as desired. It is also contemplated that the bra liner 50 does not incorporate the inserts 62 and the flaps 64.

Figure 5:
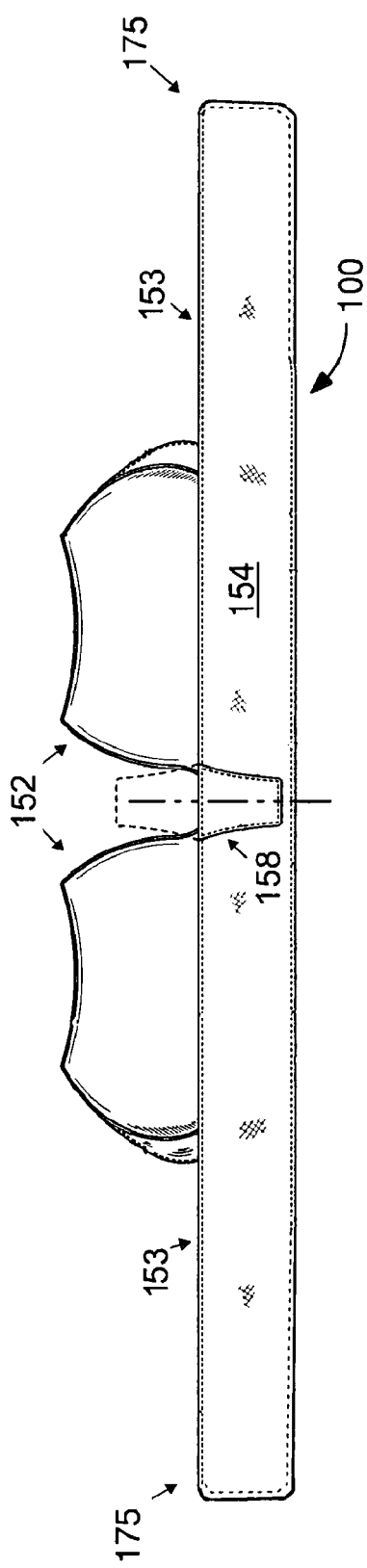
FIG. 5 is a rear elevation view of another embodiment of the present invention.
Figure 6:
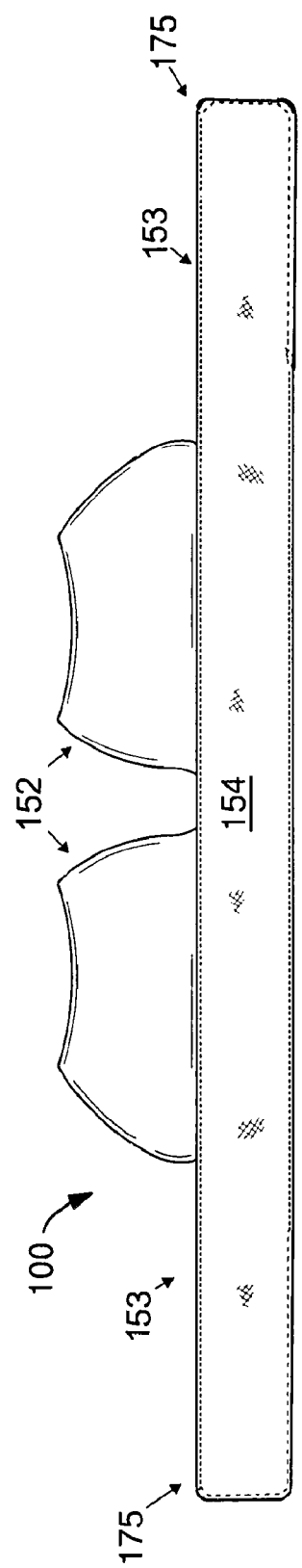
FIG. 6 is a front elevation view of the embodiment of FIG. 5

A further embodiment 100 of the present invention is depicted in FIGS. 5 and 6. This alternative embodiment functions similarly to the embodiment portrayed in FIGS. 1-4, but does not include bands 56. Further, the bra liner 100 comprises round corners 175 at the termination of strip 154. In this embodiment, the cup liners 152 and tab 158 attach directly to the upper edge 153 of the strip 154.

The material used in the embodiments of the present invention in its entirety or individual component members thereof, may comprise irritation mitigating material, perspiration or fluid absorbent material, elastic material, padding, and other material sufficient to provide the embodiments described above. Particular material such as cotton, cotton blends and organic or non-allergenic material may be used for all or portions of the various embodiments of the present invention.

The embodiments discussed herein may provide different sizing from small to extra large, and offer extended length to accommodate users who wish to extend the liner to farther under the bra side straps to extend to the back of the torso. The embodiments discussed herein may also be adapted for use with nursing bras that may be used in accordance with the opening afforded by the front edge of the cup liner portion.

Figure 7:
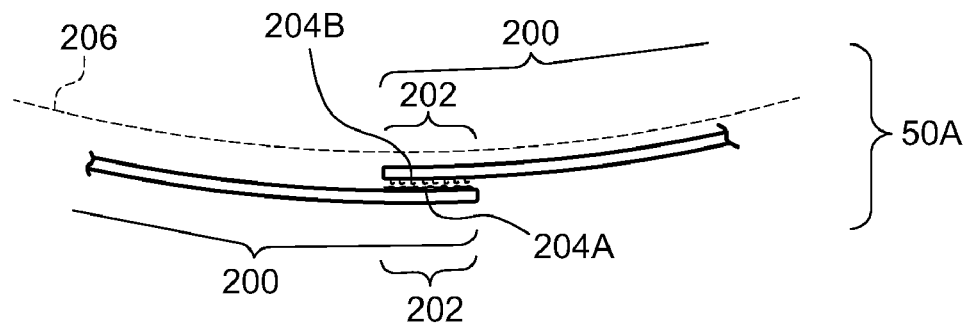
FIG. 7 is a top view of a fastenable liner wherein terminal end portions are attachable to each other.

As a further alternative, referring now to FIGS. 1 and 2, the distal end portions 200 of the strip 54 and the material bands 56 may alternatively be fabricated from a single layer stretch material. Terminal end portions 202 (see FIG. 7) of the distal end portions 200 may have mating fasteners 204A, B as shown in FIG. 7. The distal end portions 200 may be sufficiently long such that the terminal end portions 202 may reach behind the female 206 and be attachable to each other to secure the fastenable liner 50A to the female's torso.

Figure 7A:
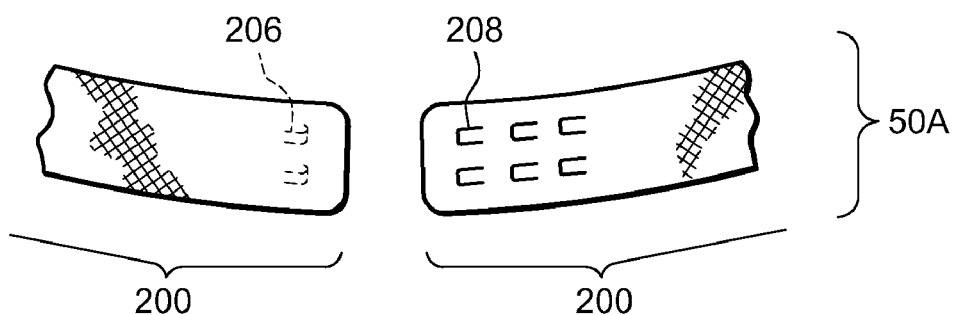
FIG. 7A is an illustration of hooks and eyelets for attaching the terminal end portions of the fastenable liner to each other.

The fasteners may be hooks 206 and eyelets 208, as shown in FIG. 7A. The hooks 206 may engage eyelets that are disposed along the length of the distal end portions 200. In this manner, the female may attach the hook 206 to any one of the eyelets 208 by stretching the distal end portions 200 to fit the body size of the female. Other types of fasteners are also contemplated. By way of example and not limitation, the fasteners 204A, B may be mating hooks 210 and loops 212 (see FIG. 7B), buttons 214 and button holes 216 (see FIG. 7C), mating snaps 218, 220 (see FIG. 7D) and/or adhesive. It is also contemplated that the terminal end portions 202 may be permanently attached to each other. By way of example and not limitation, the terminal end portions 202 of the distal end portions 200 may be sewn 222 together (see FIG. 7E).

Figure 7B:
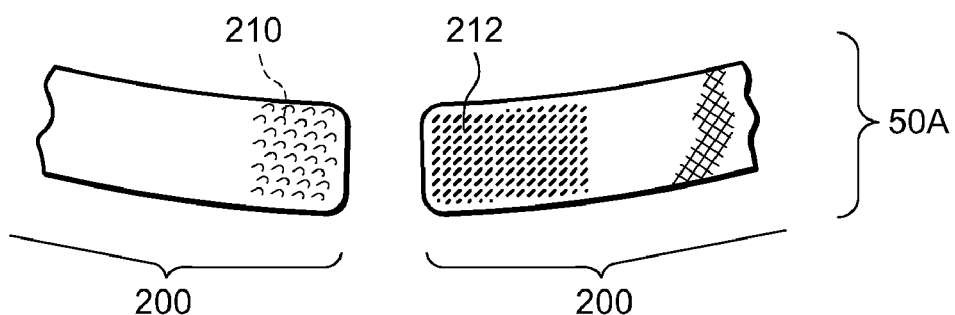
FIG. 7B is an illustration of hooks and loops for attaching the terminal end portions of the fastenable liner to each other.
Figure 7C:
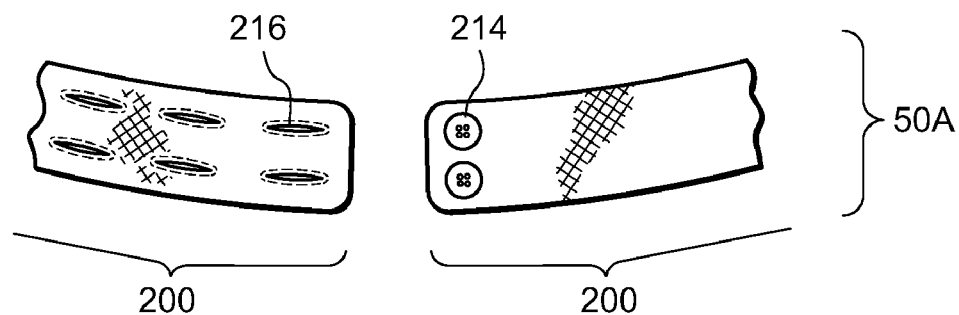
FIG. 7C is an illustration of buttons and button holes for attaching the terminal end portions of the fastenable liner to each other.
Figure 7D:
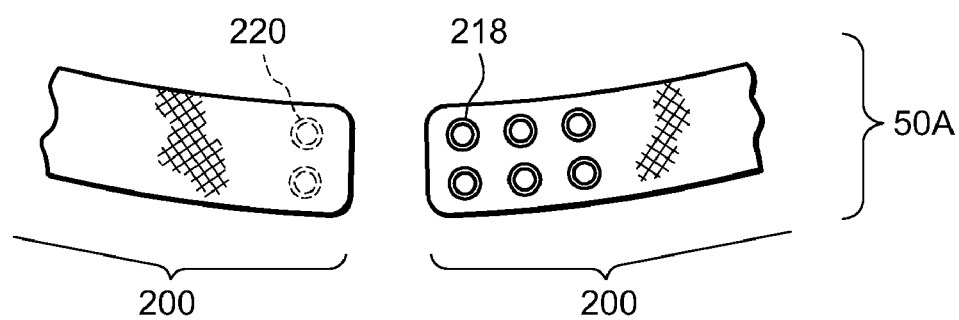
FIG. 7D is an illustration of snaps for attaching the terminal end portions of the fastenable liner to each other.
Figure 7E:
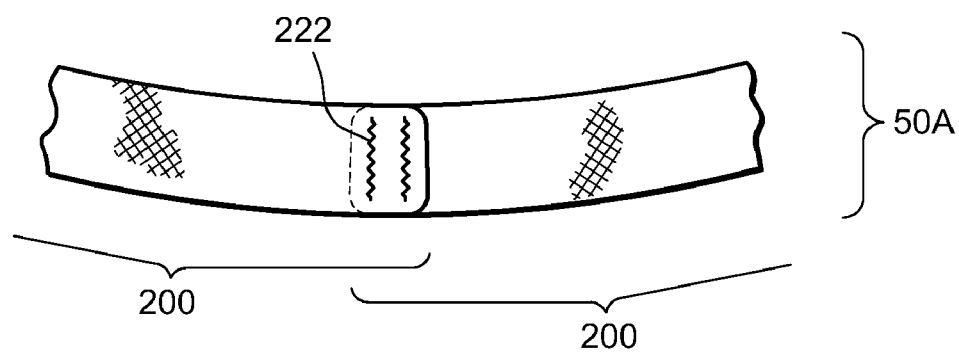
FIG. 7E is an illustration of the terminal end portions of the fastenable liner permanently sewn to each other.

Referring FIG. 7A, the hooks 206 can be selectively attached one of the eyelets 208 by stretching the distal end portions 200 to fit the body size of the female. Referring to FIG. 7B, the distal end portions 200 can be stretched then the hooks 210 attached to the loops 212 to custom fit the braless liner 50A to the body size of the wearer. Referring now to FIG. 7C, the buttons 214 may be attached any of the button holes 216 by stretching the distal end portions 202 to fit the body size of the wearer. Referring now to FIG. 7D, the snaps 220 may be engaged to any one of the mating snaps 218 by stretching the distal end portions 200 to fit the body size of the wearer.

The distal end portions 200 may be fabricated from any type of material including but not limited to a stretchable fabric, spandex, cotton, paper and combinations thereof. The distal end portions 200 may be a single layer or have multiple layers to control the amount of stretch.

The benefit of the fastenable braless liner 50A is that this liner 50A will stay in position even if the female is not wearing a bra. This may be beneficial for mothers that are nursing and not wearing a bra during normal day to day activities. Also, certain females may prefer the fastenable braless liner 50A over the non-fastenable liner 50. Additionally, small busted females may prefer the fastenable braless liner 50A over the non fastenable liner 50 since it is easier to maintain the position of the fastenable braless liner 50A during normal day to day activities. The fastenable braless liner 50A may also provide additional comfort for females who have had surgery and cannot wear a bra during recovery. Additionally, females may prefer to wear the fastenable braless liner 50A when wearing strapless clothing.

The material used in the embodiments of the liner 50A in its entirety or individual component members thereof, may comprise irritation mitigating material, perspiration or fluid absorbent material, elastic material, padding, and other material sufficient. Particular material such as cotton, cotton blends and organic or non-allergenic material may be used for all or portions of the liner 50A.

The liner 50A discussed herein may provide different sizing from small to extra large, and offer extended length to accommodate users who wish to extend the liner 50A farther under the bra side straps to extend to the back of the torso. The liner 50A discussed herein may also be adapted for use with nursing bras that may be used in accordance with the opening afforded by the front edge of the cup liner portion.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A breast covering garment liner, comprising:
   an elongated thin material strip having end portions that are attachable to each other for securing the liner to a torso of a wearer, a length of the strip being greater than a material strip width to provide a first and an opposing second side therealong, and an upper edge and lower edge along said length;
   a pair of material members having a length and a first edge attached to said first side of said elongated material strip disposed substantially symmetrically outward from said upper edge, said members disposed on lower sides of breasts of the wearer, said members each having a width between said first edge and a second edge substantially opposite said first edge, the second edge dimensioned to extend below a breast nipple of the wearer for avoiding contact with a breast nipple of the wearer.

2. The liner of claim 1, further comprising a pair of flaps each attached to said first edge of said strip and to said second end of a corresponding one of said pair of members, the flap together with said corresponding one of said pair of members forming a pocket.

3. The liner of claim 2, further comprising an insert disposed on a member and at least partially within said member pocket.

4. The liner of claim 1, wherein at least one of said strip, member, tab and flap comprises an absorbent material.

5. The liner of claim 1, wherein said of material members comprise a width and a length, wherein said width is less that said length.

6. The liner of claim 1, wherein said material members comprise an arcuate edge.

7. The liner of claim 1, further including a foldable seam thereon.

8. The liner of claim 1 wherein the end portions are removeably attachable to each other.

9. The liner of claim 1 wherein the end portions are permanently attached to each other.

10. The liner of claim 1 wherein the strip is fabricated from a stretch material.

11. The liner of claim 10 wherein the end portions are removably attachable to each other through any one of the following fasteners selected from the group consisting of hooks and eyelets, hooks and loops, buttons and button holes, snaps, adhesives and combinations thereof.

12. The liner of claim 1 further comprising a pair of bands each attached to a respective material member and along the length of the elongated thin material strip.

13. The liner of claim 1 further comprising a tab having an edge joined to said strip first side, and partially overlapping said member first edges, and disposed to be foldable away from said member first edges and toward said strip second side.

14. The liner of claim 13 wherein the tab, elongated thin material strip and the pair of material members are fabricated from a wicking material.

15. The liner of claim 1 wherein the second edge is concave.

16. A breast covering garment liner, comprising:
   a pair of liner members;
   a strip defining a length, the strip connected to said liner members along one side of said length and having a space between the liner members, end portions of the strip being attachable to each other for securing the liner to a torso of a wearer;
   an insert and
   an insert retainer disposed on said liner member.

17. The liner of claim 16 wherein at least a portion of the liner member is fabricated from any one of the following materials selected from the group consisting of an irritation mitigating material, perspiration absorbent, fluid absorbent, elastic material, padding material, support material, prosthesis material, organic material, non-allergenic material, cotton material, cotton blend material and combinations thereof.

18. A breast covering garment liner, comprising:
   a pair of liner members;
   a strip defining a length, the strip connected to said liner members along one side of said length and having a space between the liner members, end portions of the strip being attachable to each other for securing the liner to a torso of a wearer; and
   a foldable tab connected to said strip and disposed to selectively overlay said space.

19. The liner of claim 18 wherein the liner members, strip and the tab are fabricated from a wicking material.

* * * * *